(12) United States Patent
Wu

(10) Patent No.: US 10,161,897 B2
(45) Date of Patent: Dec. 25, 2018

(54) SENSORS INCORPORATING PALLADIUM ELECTRODES

(71) Applicant: Xerox Corporation, Norwalk, CT (US)

(72) Inventor: Yiliang Wu, Oakville (CA)

(73) Assignee: XEROX CORPORATION, Norwalk, CT (US)

(*) Notice: Subject to any disclaimer, the term of this patent is extended or adjusted under 35 U.S.C. 154(b) by 340 days.

(21) Appl. No.: 14/593,111

(22) Filed: Jan. 9, 2015

(65) Prior Publication Data
US 2016/0202202 A1 Jul. 14, 2016

(51) Int. Cl.
G01N 27/28 (2006.01)
G01N 27/30 (2006.01)

(52) U.S. Cl.
CPC .................. *G01N 27/302* (2013.01)

(58) Field of Classification Search
CPC .............. G01N 27/302; G01N 27/28
See application file for complete search history.

(56) References Cited

U.S. PATENT DOCUMENTS

| | | | | |
|---|---|---|---|---|
| 3,272,725 A | * | 9/1966 | Garst | G01N 27/404 204/402 |
| 3,709,810 A | * | 1/1973 | Grubb | G01N 27/333 204/416 |
| 5,320,735 A | * | 6/1994 | Kato | G01N 27/333 204/192.1 |
| 5,352,352 A | * | 10/1994 | Tsukada | A61B 5/14539 204/414 |
| 6,572,748 B1 | * | 6/2003 | Herrmann | G01N 27/301 204/408 |
| 2001/0042693 A1 | * | 11/2001 | Onitskansky | G01N 27/49 205/780 |
| 2002/0180609 A1 | * | 12/2002 | Ding | G01N 27/333 340/633 |
| 2013/0091924 A1 | * | 4/2013 | Scheffler | G01N 33/007 73/23.3 |

* cited by examiner

*Primary Examiner* — Susan D Leong
(74) *Attorney, Agent, or Firm* — Fay Sharpe LLP

(57) ABSTRACT

A pH sensor contains a potentiometric sensing electrode made of palladium. An optional metal oxide layer may be coated on the palladium electrode to enhance sensitivity. The pH sensor has high sensitivity, a shorter response time, and good reversibility and stability.

9 Claims, 3 Drawing Sheets

SENSORS INCORPORATING PALLADIUM ELECTRODES

BACKGROUND

The present disclosure relates to pH sensors incorporating palladium electrodes and processes for manufacturing such sensors. They find particular application in conjunction with the biochemical and biological arts, and will be described with particular reference thereto. The pH sensors are suitable for use in applications such as wearable biomedical electronic devices.

Wearable biomedical electronic devices have recently attracted extensive research attention, as these devices could be of extreme importance in both early diagnosis through continuous monitoring of complex health conditions and in patients undergoing treatments. The pH value is a very useful indicator for disease diagnostics, medical treatment optimization, and constant monitoring of biochemical and biological processes of the human body. Therefore, developing highly reliable and conformable pH sensors for future wearable biomedical electronic devices is desired.

Although there are many different portable pH sensors available, in view of their rates of power consumption, architecture, and cost, they are not suitable for future wearable electronic applications. One promising direction is to use metal or metal oxide based sensing electrodes through the well-known and simple potentiometric method for pH sensing. Such metal or metal oxide sensors provide the advantages of simple structure design, low manufacturing costs, compatibility with miniaturization processes, and high sensitivity.

Gold is often used in electrodes for metal or metal oxide based pH sensors. Although gold itself shows some pH sensitivity (typically 23-26 mV/pH), metal oxides such as $TiO_2$, $ZnO$, $WO_3$, $SnO_2$, $RuO_2$, $Ta_2O_5$, $PdO$, or $IrO_2$ are often coated on gold electrodes to increase sensitivity.

It would be desirable to produce pH sensors that have electrodes made from a lower-cost alternative metal to gold, but still show comparable or better pH sensitivity to sensors with gold electrodes.

BRIEF DESCRIPTION

Disclosed in various embodiments are pH sensors comprising palladium electrodes. The sensors comprise a sensing electrode, a counter electrode, and an electrolyte layer, which is sandwiched between the sensing electrode and the counter electrode. The sensing electrode is formed by solution processing and comprises palladium.

Disclosed in various embodiments are pH sensors comprising: (a) a sensing electrode; (b) a counter electrode; and (c) an electrolyte layer; wherein the electrolyte layer is located between the sensing electrode and the counter electrode; and wherein the sensing electrode comprises palladium.

The sensing electrode may have access holes to expose the electrolyte layer. The sensing electrode can be prepared from a thermally decomposable palladium precursor composition. The sensing electrode may comprise at least 50 atomic percent of palladium oxide on its surface.

The electrolyte layer may be in physical contact with the sensing electrode and the counter electrode.

The counter electrode may comprise silver and silver chloride.

The pH sensor may have a sensitivity of at least 40 mV/pH. In other embodiments, the pH sensor has a response time of no longer than 200 seconds. In still other embodiments, the pH sensor has a linearity of at least 95% in the pH range from 2 to 12.

In some embodiments, the pH sensor further comprises an insulator located adjacent to the electrolyte layer and between the sensing electrode and the counter electrode. In others, the pH sensor further comprises a metal oxide layer located between the sensing electrode and the electrolyte layer. The metal oxide layer can be $TiO_2$, $ZnO$, $WO_3$, $SnO_2$, $RuO_2$, $Ta_2O_5$, $PdO$, or $IrO_2$.

Also disclosed are biomedical devices comprising the pH sensor described above. Such devices can be wearable, for example on the arm or leg.

Also disclosed are processes for manufacturing a pH sensor comprising: solution coating an object with a palladium precursor composition to form an amorphous coating on the object; heating the amorphous coating to form a palladium sensing electrode; affixing the sensing electrode to one surface of an electrolyte layer; and affixing a counter electrode to an opposite surface of the electrolyte layer.

The solution coating can be performed by spin coating, dip coating, spray coating, flexographic printing, offset printing, aerosol jet printing, or inkjet printing the palladium precursor composition onto the substrate. The heating can be performed at a temperature from about 195 degrees to about 300 degrees Celsius for a period of about 2 minutes to 48 hours.

The palladium precursor composition may have a viscosity of about 30 to about 32 cps at 25 degrees Celsius. The counter electrode can comprise solid silver and silver chloride.

The processes may further comprise making access holes in the palladium sensing electrode. Sometimes, the processes further comprise placing an insulator next to the electrolyte layer and between the sensing electrode and the counter electrode. The processes can also further comprise forming a metal oxide layer between the sensing electrode and the electrolyte layer. The heating can be done in air or in an oxygen atmosphere.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
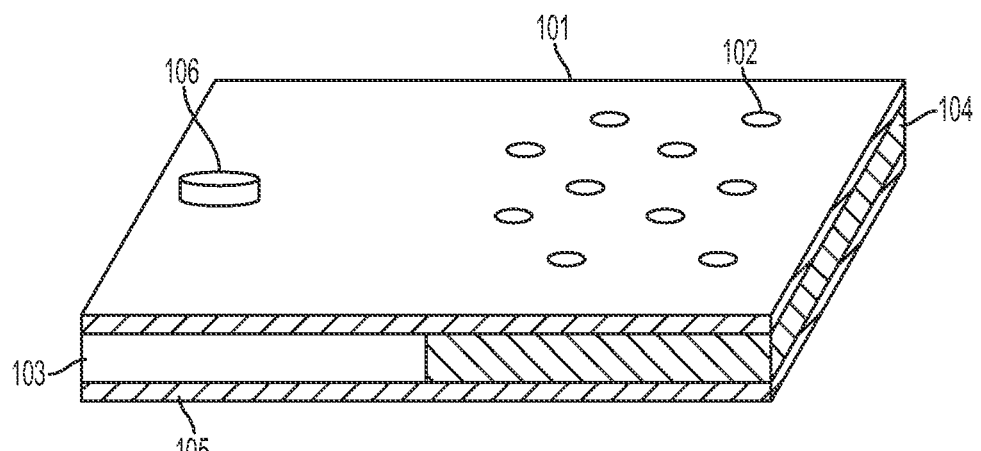
FIG. 1 is an isometric view of an exemplary embodiment of a pH sensor.

A more complete understanding of the components, processes and apparatuses disclosed herein can be obtained by reference to the accompanying drawings. These figures are merely schematic representations based on convenience and the ease of demonstrating the present disclosure, and are, therefore not intended to indicate relative size and dimension of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The term "room temperature" refers to a temperature of about 23 degrees Celsius.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The use of the singular terms "a", "an", and "the" should be construed to include plural referents as well, unless clearly indicated otherwise by the context. Put another way, these singular terms should be construed as "at least one".

The present disclosure relates to a sensor assembly comprising two electrodes and an electrolyte layer located between the electrodes. At least the sensing electrode comprises palladium. The sensor assembly is used to measure the pH value of a liquid.

The pH value refers to the acidity or alkalinity of a liquid, with a value of indicating high acidity and a value of 14 indicating high alkalinity. Within the human body, balanced pH levels are indicative of homeostasis. Extreme pH values (either low or high) can denature enzymes or destabilize proteins, leading to a variety of health problems, including irregular heart rates and neural firing. Other degenerative diseases include diabetes, cancer, cardiovascular disease and excessive systemic weight gain. Sensors that can determine the pH would be useful.

A typical pH sensor is made up of three components: the pH sensor (including a sensing/measuring electrode, a reference/counter electrode, and a temperature sensor), a pre-amplifier, and an analyser or transmitter. The sensing electrode, which is sensitive to hydrogen ions, develops a potential (voltage) directly related to the hydrogen concentration of the solution being measured, and the counter electrode provides a stable potential against which the sensing electrode can be compared.

In potentiometric sensors, the signal is measured as the potential difference (voltage) between the sensing electrode and the counter electrode when no current is flowing. Only the material being measured needs to pass between the electrodes. Essentially, a known voltage on the counter electrode is used as a comparison to the voltage that changes on the sensing electrode. These voltage changes occur when a solid electrolyte compound between the two electrodes obtains an electrical charge as a liquid or gas in the form of an ionic conductor passes by. The level of charge is used to determine the quantity of ions present. Ion-selective electrodes that can sense particular ions, such as fluorine or iodine, are particularly selective and are commonly available for use in potentiometric applications.

The use of palladium electrodes, as disclosed in the present disclosure, allows for a simpler pH sensor structure design, easier miniaturization, improved sensitivity, better reliability due to better adhesion and mechanical strain resistance of palladium, and lower manufacturing costs due to the lower costs of raw materials and a simpler fabrication process by printing.

Figure 2:
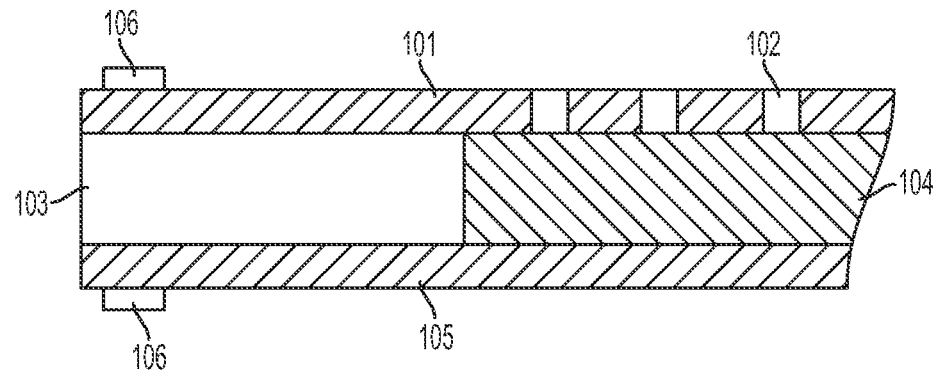
FIG. 2 is a cross-sectional side view of the pH sensor of FIG. 1.
Figure 3:
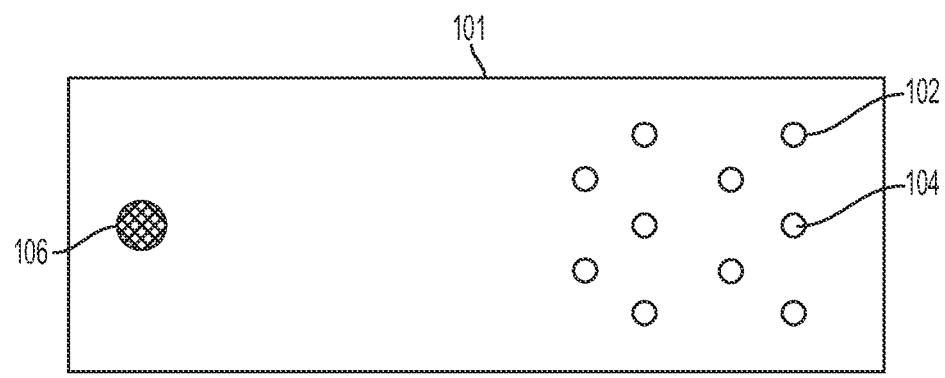
FIG. 3 is a top view of the pH sensor of FIG. 1.

FIG. 1, FIG. 2, and FIG. 3 illustrate an exemplary embodiment of a pH sensor. FIG. 1 is a perspective view, FIG. 2 is a side cross-sectional view, and FIG. 3 is a top (plan) view of the sensor.

The pH sensor includes a palladium sensing electrode 101, an electrolyte layer 104, and a counter electrode 105, which form three separate layers. The sensing electrode 101 and the counter electrode 105 are both in electrical contact with the electrolyte layer 104, but do not contact each other. As illustrated here, the sensing electrode 101 and the counter electrode 105 are on opposite sides of the electrolyte layer 104, or put another way the electrolyte layer 104 is sandwiched between the sensing electrode 101 and the counter electrode 105. An insulator 103 is located adjacent to an end of the electrolyte layer 104, and is also sandwiched between the sensing electrode 101 and the counter electrode 105. The portion of the sensing electrode adjacent the electrolyte layer may include access holes 102 going entirely through the sensing electrode layer, and permits fluid to directly contact the electrolyte layer 104. As illustrated here, the access holes 102 are on one end of the sensing electrode layer, and the other end does not contain any such access holes. The electrolyte layer can be a gel or a solid. Electrically conductive leads 106 are used to apply and measure voltage across the electrodes.

If desired, a metal oxide layer (not shown) can also be coated onto the palladium sensing electrode to increase its sensitivity. The metal oxide layer would be located between the sensing electrode 101 and the electrolyte layer 104. The metal oxide can be $TiO_2$, $ZnO$, $WO_3$, $SnO_2$, $RuO_2$, $Ta_2O_5$, $PdO$, or $IrO_2$.

The sensing electrode, and optionally the counter electrode, is prepared from a thermally decomposable palladium precursor, which can be used with liquid-based deposition processes to make a palladium layer on an object or a substrate. The palladium precursor compositions comprise a palladium salt, and an organoamine, and are substantially free of water. In other embodiments, the palladium precursor compositions are substantially free of water and substantially free of reducing agent. In some embodiments, the organoamine functions as both a complexing agent and a solvent. In other embodiments, the organoamine functions as a complexing agent only, and the palladium precursor composition can further comprise a second organic solvent. In specific embodiments, the organoamine functions as a complexing agent only, and the palladium precursor composition can further comprise a second organic solvent which is immiscible with water. In other specific embodiments, the organoamine functions as both a complexing agent and a solvent, and the palladium precursor composition can further comprise a second organic solvent. These precursor compositions can be processed into palladium layers with high conductivity and good adhesion at low temperatures. In particular embodiments, the palladium precursor compositions consist essentially of the palladium salt and at least one organoamine. In other particular embodiments, the palladium precursor compositions consist essentially of the palladium salt, at least one organoamine, and a water immiscible organic solvent.

The palladium salt may be selected from the group consisting of palladium carboxylate, palladium chloride, palladium nitrate, palladium sulfate, palladium iodide, palladium cyanide, ethylenediamine palladium chloride, tetraaminepalladium bromide, bis(acetylacetonato) palladium, diamine dinitro palladium, or mixtures thereof. In specific embodiments, the palladium salt is palladium acetate.

In some embodiments, the palladium salt is a palladium carboxylate having a general structure of $Pd(OOCR^1)_x(OOCR^2)_{2-x}$, wherein $R^1$ and $R^2$ are independently selected from hydrogen, alkyl having 1 to 11 carbon atoms, alkenyl having 2 to about 13 carbon atoms, and alkynyl having 2 to about 13 carbon atoms. Hydrogen atoms on $R^1$ or $R^2$ may be substituted with another functional group such as —CHO, —OH, halogen, and the like. In specific embodiments, the palladium carboxylate is palladium acetate, $Pd(O—CO—CH_3)_2$. The number x can be any number from 0 to 2, for example, 0, 0.01, 0.1, 1, 1.5, 1.57, 2.0, and the like. In preferred embodiments, the palladium salt is a palladium carboxylate.

The term "alkyl" refers to a radical composed entirely of carbon atoms and hydrogen atoms which is fully saturated and of the formula —$C_nH_{2n+1}$. The alkyl radical may be linear, branched, or cyclic.

The term "alkenyl" refers to a radical composed entirely of carbon atoms and hydrogen atoms which contains at least one carbon-carbon double bond. An alkenyl radical may be linear or branched. Aromatic rings are not considered to be alkenyl.

The term "alkynyl" refers to a radical composed entirely of carbon atoms and hydrogen atoms which contains at least one carbon-carbon triple bond.

It should be noted that the palladium salt is a molecular compound. Pd—Pd bonds may be present in the molecular compound. However, the palladium salt should not be considered to be a nanoparticle or similar material. The palladium atom in the salt is not zero valent, while palladium atoms are zero valent in the nanoparticle form.

The organoamine may function as a complexing agent. Generally, the organoamine may be any primary, secondary, or tertiary amine. The organoamine can also be a monoamine, diamine, or polyamine. Combinations of more than one organoamine are also contemplated. More specifically, the organoamine may contain one, two, or more amine groups of Formula (I):

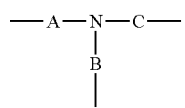

Formula (I)

wherein A, B, and C are independently selected from hydrogen and an organic group, and at least one is an organic group. When the tertiary amine contains more than one such amine group, the nitrogen atoms are not directly bonded to each other. An organic group contains at least one carbon atom. Exemplary organic groups include alkyl, aryl, substituted alkyl, and substituted aryl. Any two of organic groups A, B and C can form a cyclic structure.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "substituted" refers to at least one hydrogen atom on the named radical being substituted with another functional group, such as halogen, hydroxyl, mercapto (—SH), —CN, —$NO_2$, —COOH, and —$SO_3H$. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl or heteroaryl group may also be substituted with alkyl or alkoxy. Exemplary substituted aryl groups include methylphenyl and methoxyphenyl.

Some specific examples of organoamines include ethylamine, propylamine, butylamine, pentylamine, hexylamine, heptylamine, octylamine, nonylamine, decylamine, undecylamine, dodecylamine, tridecylamine, tetradecylamine, hexadecylamine, diaminobutane, diaminopentane, diaminohexane, diaminoheptane, diaminooctane, diaminononane, diaminodecane, dipropylamine, dibutylamine, dipentylamine, dihexylamine, diheptylamine, dioctylamine, dinonylamine, didecylamine, methylpropylamine, ethylpropylamine, propylbutylamine, ethylbutylamine, ethylpentylamine, propylpentylamine, butylpentylamine, triethylamine, tributylamine, and trihexylamine.

In more specific embodiments, the organoamine(s) present in the palladium precursor composition is immiscible in water. Generally, water immiscible organoamines contain at least 8 carbon atoms per amine group. In particular embodiments, the organoamine has only one nitrogen atom (i.e. a monoamine). Exemplary water immiscible organoamines include primary aliphatic amines of the formula $NH_2—R^3$, where $R^3$ is alkyl having from 8 to about 18 carbon atoms, especially those where the $R^3$ is a linear alkyl chain. Some secondary aliphatic amines are also water immiscible, such as those of the formula $NHR^4R^5$, where $R^4$ and $R^5$ are independently alkyl having from 4 to about 18 carbon atoms. Some tertiary aliphatic amines are also water immiscible, such as those of the formula $NR^6R^7R^8$, where $R^6$, $R^7$, and $R^8$ are independently alkyl having from 3 to about 18 carbon atoms.

Examples of water immiscible organoamines include octylamine, nonylamine, decylamine, undecylamine, dodecylamine, tridecylamine, tetradecylamine, hexadecylamine, dipentylamine, dihexylamine, diheptylamine, dioctylamine, dinonylamine, didecylamine, propylpentylamine, butylpentylamine, tributylamine, and trihexylamine.

In embodiments, the organoamine also functions as a solvent, with the palladium salt being "dissolved" in the organoamine. The organoamine should thus be in the liquid phase. Due to the different melting points for various organoamines, the temperature of the palladium precursor composition may be greater than room temperature. For example, dodecylamine has a melting point of 28-30° C., hexadecylamine has a melting point of 43-46° C., and octadecylamine has a melting point of 53° C. In some embodiments, the organoamine has a melting point less than 50 degree C., or a melting point of less than 40 degree C., including a melting point less than room temperature. In other words, the organoamine is a liquid at room temperature. Some examples of organoamines that are liquid at room temperature include octylamine (mp=−1° C.), diaminopropane (mp=−12° C.), and tripropylamine (mp=−94° C.). The liquid phase/low melting point is important to achieve a uniform palladium layer. After liquid depositing the precursor composition, an amorphous layer will be formed if an organoamine with a low melting point is used. On the other hand, an organoamine with a high melting point will crystallize out after deposition of the precursor composition, which may cause high surface roughness and holes in the final palladium layer. In embodiments, the temperature of the palladium precursor composition may be from room temperature up to about 80° C. This temperature may occur with no external heat source, for example due to an exothermal reaction between the palladium salt and the organoamine.

In some embodiments, the organoamine is not an amino acid compound. In other words, with reference to Formula (I), none of A, B, or C are substituted with a —COOH group. In some other embodiments, the organoamine can be an amino acid compound (i.e. at least one of A, B, and C is substituted with —COOH).

In more specific embodiments, the organoamine is a primary monoamine, i.e. a compound of the formula $NH_2$—$R^3$, where $R^3$ is alkyl having from about 2 to about 18 carbon atoms, including from about 5 to about 14 carbon atoms, or from 8 to about 18 carbon atoms.

Without being limited by theory, it is believed that the palladium salt and the organoamine form a palladium amine complex. This is usually evidenced by a color change. For example, palladium acetate is a reddish solution in toluene, but when an organoamine such as octylamine is added, the solution changes into a light yellow color. The palladium amine complex helps to dissolve the palladium salt, permitting high loading of the salt, and as a result, a high palladium content in the precursor composition. In embodiments, the palladium amine complex is dissolved, and the resulting precursor composition is a clear solution. It should be noted that the composition may also comprise non-complexed palladium salt molecules. In specific embodiments, the composition comprises the palladium amine complex and an excess amount of the organoamine in non-complexed form.

In other specific embodiments, the palladium amine complex is formed from a monoamine. In particular, the monoamine may be a primary alkyl monoamine of the formula $NH_2$—$R^3$, where $R^3$ is alkyl having at least 8 carbon atoms.

The palladium and organoamine in the precursor composition form a complex. It should be noted that palladium is sometimes used as a catalyst in organic synthesis. When an organic synthesis reaction contains an organoamine reagent, a palladium organoamine complex might be formed in an organic reaction. This differs from the present disclosure in several aspects. First, the palladium in a synthesis reaction functions as a catalyst, while the palladium in the present precursor composition provides a metal source for a palladium layer, and does not act as a catalyst. Second, the organoamine in a synthesis reaction functions as a reactant, while the organoamine in the precursor composition functions as a complexing agent and/or solvent. Third, palladium is used in a catalytic amount in those synthesis reactions, while palladium salt is merely one of the dominant components of the precursor composition. In general, here the precursor composition is a non-catalytic composition. Stated differently, the palladium amine complex is not used in forming a product from two reactants. The term "non-catalytic" refers to the fact that the palladium in the palladium precursor composition does not function as a catalyst. This can be seen in that the organoamine does not become part of a third compound in the precursor composition. In other words, the palladium precursor composition does not contain any compounds which become covalently coupled to the organoamine.

In embodiments, the molar ratio of the organoamine to the palladium salt is from about 1:1 to about 10:1. In more specific embodiments, the molar ratio of organoamine to palladium salt is from about 1:1 to about 5:1, or from about 2:1 to about 5:1, or from about 2:1 to about 3:1. In some embodiments, the molar ratio of the organoamine to the palladium salt is at least 2:1 to ensure good dissolution of the palladium salt in the organoamine.

In other specific embodiments, particular combinations of palladium salt and organoamine are contemplated. In these combinations, the total number of carbon atoms in the palladium salt and organoamine are combined, and their total is 10 or higher. For example, if the palladium salt is palladium carboxylate $Pd(OOCR^1)_x(OOCR^2)_{2-x}$, and the organoamine is octylamine $H_2N$—$R^3$, then the total number of carbon atoms is the carbon atoms in $R^3$+carbon atoms in $R^1$ times X+carbon atoms in $R^2$ times (2-X)+2. As a specific example, if the palladium salt is palladium acetate $Pd(OCOCH_3)_2$ and the organoamine is octylamine, then the total number of carbon atoms is 12, four from the acetate and eight from the organoamine. The total number is based on the chemical formulae for the palladium salt and organoamine. The total number does not change with differences in the relative amounts of the palladium salt and organoamine, and is not related to the number of moles or the weight percentages of the two ingredients. In other embodiments, the total number of carbon atoms in the palladium salt and organoamine is at least 10, or at least 11, or at least 12.

In embodiments, another organic solvent which is immiscible with water can be included, or in other words a second water immiscible organic solvent can be used. When a given organic solvent is mixed with water at about equal amounts by volume, if a phase separation is detected (either visually or by instruments such as light scattering or refractive index) after settling, the solvent is considered to be water immiscible. The palladium salt, the organoamine, and the resulting palladium amine complex should be soluble in this second solvent. For example, at least 0.5 wt % of the amount of the given component added to the second solvent should dissolve, including at least 1 wt %, or at least 10 wt % of the amount added. The non-soluble portion can be removed from the precursor composition by, for example, filtration.

Any suitable water immiscible organic solvent can be used for the second solvent. In some embodiments, the second organic solvent may be a hydrocarbon solvent, for example a substituted hydrocarbon or an aromatic hydrocarbon solvent. Specifically, the hydrocarbon solvent has at least 6 carbon atoms, from 6 to about 25 carbon atoms. Exemplary solvents include toluene, xylene, mesitylene, ethylbenzene, diethylbenzene, trimethyl benzene, methyl ethylbenzene, tetrahydronaphthalene, chlorobenzene, dichlorobenzene, trichlorobenzene, chlorotoluene, and the like, or mixtures thereof. In other embodiments, the second organic solvent is a ketone, ester, ether, and the like. Exemplary solvents include methyl isobutyl ketone, methyl benzoate, benzyl benzoate, anisole, cyclohexanone, acetophenone, and the like. In some embodiments, the second organic solvent has a boiling point at least 80° C., including at least 100° C. In some specific embodiments, the second solvent has a high boiling point at least 150° C.

In particular embodiments, the palladium precursor composition should not contain any water. In other words, the palladium precursor composition fails to include water, or is substantially free of water. However, it should be noted that these phrases do not require an absolute absence of water. Some residual water may be present in the precursor composition from the various ingredients or from ambient/ atmospheric conditions. For example, octylamine is typically sold with a specification of maximum 0.1 wt % water content, or tributylamine is typically sold with a specification of maximum 0.3 wt % water content. These amounts of water should be considered to be residual and precursor compositions containing such amounts of water should be considered substantially free of water.

In some other embodiments, water and/or a water miscible solvent may be present in the palladium precursor composition. However, the amount of water and/or water miscible solvent (by weight) is in some embodiments less than the amount of organoamine. Exemplary water miscible solvents include alcohols such as methanol, ethanol, propanol, and butanol; glycols, acetone, tetrahydrofuran (THF), dichloromethane, ethyl acetate, dimethylformamide (DMF), dimethyl sulfoxide (DMSO), acetic acid, acetonitrile, and dioxane. Any suitable concentration of the water and/or water miscible solvent(s) may be present.

The palladium salt typically makes up from about 1 to about 50 weight percent (wt %) of the precursor composition. In more specific embodiments, the palladium salt makes up from about 5 wt % to about 30 wt % of the precursor composition.

The precursor composition can further include another metal species, for example silver (Ag), gold (Au), copper (Cu), nickel (Ni), rhodium (Rh), cobalt (Co), zinc (Zn), platinum (Pt), and the like. The other metal species may be introduced as another starting ingredient, for example in the form of a metal salt. For example, silver acetate can be used in combination with palladium acetate to form a Ag—Pd alloy. The additional metal salt in the composition can be present in an amount of, for example, from about 0.1 wt % to about 40 wt %, including from about 1 wt % to about 20 wt % of the precursor composition. However, the additional metal salt should be less than the amount of the palladium salt.

The palladium precursor composition has a surface tension of less than 33 mN/m, including less than 30 mN/m, or less than 28 mN/m, or for example from about 23 mN/m to about 30 mN/m. This low surface tension enables a uniform coating of palladium to be formed on the substrate. The selection of a suitable organoamine or second water-immiscible organic solvent provides the desired surface tension. The palladium precursor composition has a viscosity from about 0.8 to about 100 cps, including from about 0.8 to about 50 cps, or about 2 to about 35 cps. In particular embodiments, the palladium precursor composition has a viscosity of about 30 to 32 centipoise (cps) at 25 degrees Celsius.

In certain embodiments, the palladium precursor composition does not contain a reducing agent, or is substantially free of reducing agent. Some examples of such reducing agents include formic acid and formic acid salts or esters, hypophosphites, hydrazines, ammonium compounds, amine borane compounds, alkali metal borohydrides, oxalic acid, alkali or alkaline earth sulfites, and the like.

The palladium precursor composition can be used to form the sensing electrode 101 via solution deposition. "Solution depositing" and "solution processing" refer to a process where a liquid is deposited upon a substrate to form a structure. This is in contrast to vacuum depositing processes. The present processes for forming a palladium structure are also different from other solution-based processes, for example electroplating, which requires a plate to remain immersed in a solution and also requires exposure to an electric current to form a metal coating on the plate. The present processes also offer several advantages compared to electroless plating. In electroless plating, the deposition of the palladium is slow, so that the overall plating process takes much longer than the solution deposition processes of the present disclosure. Electroless plating also generates a great deal of waste due to residual metal present in the solution. Electroless plating baths or solutions also often contain a reducing agent. In addition, the present processes allow for fine control of where the palladium is deposited for example by inkjet printing. In other words, it is easy to form a patterned palladium structure in a discrete location using the present processes. In contrast, metal deposition in electroless plating occurs over all surfaces which are immersed in the solution. Masking surfaces which are not to be plated is a complex and time-consuming procedure. However, the present processes can be used in combination with electroplating or electroless plating if needed.

Exemplary solution deposition processes include dip coating, spin coating, spray coating, flexographic printing, offset printing, aerosol jet printing, or inkjet printing (where the palladium precursor composition is ejected onto the substrate by an inkjet printhead). Certain processes involve solution depositing the substrate with the palladium precursor composition to form a structure or film on the substrate. In embodiments, the structure or film has a thickness of from about 10 nanometers to about 50 micrometers, including from about 10 nm to about 30 micrometers, or from about 50 nm to about 5 micrometers, or from about 80 nm to about 1 micrometer. For example, the electrolyte layer 104 could be used as the substrate upon which the palladium precursor composition is deposited.

The palladium precursor composition which was previously deposited is then heated to form the palladium layer on the substrate. The heating causes the palladium amine complex or palladium salt to thermally decompose to form a solid palladium layer. In contrast, in electroless plating, the palladium salt or complex is chemically reduced to palladium. The heating may be performed at a temperature of from about 195° C. to about 300° C. In other embodiments, the heating is performed at a temperature from about 200° C. to about 280° C. for about 2 minutes to about 24 hours, or from about 200° C. to about 250° C. for about 2 minutes to about 12 hours. Regardless of the substrate used, the heating temperature is desirably one that does not cause adverse changes in the properties of any previously deposited layer(s) or the substrate (whether a single layer substrate or multilayer substrate). The heating may be performed for a period of up to 30 minutes, and could be for a period as short as 0.1 seconds depending on the size of the palladium layer and the heating method. The heating can be performed in air, in an oxygen atmosphere, in an inert atmosphere (for example, under nitrogen or argon), or in a reducing atmosphere (for example, under nitrogen containing from 1 to about 20 percent by volume hydrogen). The heating can also be performed under normal atmospheric pressure or at a reduced pressure of, for example, from about 1000 millibars to about 0.01 millibars. Examples of heating techniques may include thermal heating (for example, a hot plate, an oven, and a burner), infra-red ("IR") radiation, a laser beam, flash light, microwave radiation, or UV radiation, or a combination thereof. The type of atmosphere in which the heating can be performed can depend upon whether a metal oxide layer is desired on the palladium sensing electrode, and what type of metal oxide is used. For a layer comprising palladium and palladium oxide, an air or oxygen atmosphere can be used.

It is noted that in FIG. 1, access holes 102 are present in the palladium sensing electrode 101. These holes can be formed by making holes in a palladium film after curing, or the palladium precursor composition could be deposited to form a layer having holes already present therein.

During the heating, in some embodiments, at least a portion of the palladium organoamine complex first form palladium nanoparticles in-situ. These palladium nanoparticles subsequently coalesce into a continuous and uniform palladium layer. This intermediate step where palladium nanoparticles are formed will enhance uniformity of the final palladium film. This is different from a conventional electroless plating process, where the palladium salt deposits into a palladium layer directly without going through an intermediate nanoparticle form. In further embodiments, a majority of the palladium organoamine complex forms palladium nanoparticles in-situ. The formation of palladium nanoparticles is evidenced by the color change of the deposited palladium organoamine complex upon heating. A black color is often observed prior to the formation of the silvery metallic palladium layer, indicating that a palladium nanoparticle intermediate was formed during the heating step.

It should be noted that when the palladium precursor composition is heated to form the palladium layer, the temperature of the precursor composition is increased above the temperature of the precursor composition during the solution deposition. As previously discussed, the temperature of the precursor composition may be greater than room temperature to ensure the organoamine is in the liquid phase during the solution deposition.

The deposition processes described herein can also be repeated to build up a thicker palladium layer for the sensing electrode 101. For example, in embodiments, the thickness of the final layer may also be from about 10 nanometers to about 50 micrometers, or from about 50 nanometers to about 30 micrometers, or from about 50 nm to about 5 micrometers, or from about 80 nm to about 1 micrometer. In this regard, multiple solution deposition steps may be performed, with one subsequent heating to form the final layer. Alternatively, the steps of solution deposition and heating can be repeated multiple times to build a thick layer out of several thinner layers.

In particular, it is believed that the surface roughness of the palladium layer produced using the deposition processes and the compositions described herein is less than that produced by other processes (put another way, the palladium layer has high surface smoothness). In embodiments, the resulting palladium layer of the sensing electrode 101 has a surface roughness of 50 nanometers (nm) or less, including a surface roughness of 20 nm or less, or a surface roughness of 10 nm or less. Alternatively, the ratio between the surface roughness and the thickness of the palladium layer may be in the range of 1/5 or less (i.e. 0.2:1 or less), including a range of 1/10 or less (i.e. 0.1:1 or less) or 1/20 or less (i.e. 0.05:1 or less). The surface roughness is determined by the root mean square (rms) method. Briefly, the surface roughness is measured at several points on the layer. The reported surface roughness is the square root of the arithmetic mean (average) of the squares of the measured values.

Prior to heating, the structure or film containing the palladium salt or palladium amine complex may be electrically insulating or have very low electrical conductivity. Heating results in an electrically conductive layer of palladium. The conductivity of the palladium layer produced by heating is, for example, more than about 100 Siemens/centimeter ("S/cm"), more than about 1000 S/cm, more than about 2,000 S/cm, more than about 5,000 S/cm, or more than about 10,000 S/cm or more than about 50,000 S/cm.

In some embodiments, reducing agents may not be needed to prepare and obtain the palladium layer used as the sensing electrode. Thus, such reducing agents are not present in the palladium precursor composition and are not separately added as an additional processing step.

In particular embodiments, the palladium precursor composition consists essentially of one or more palladium salts and one or more organoamines. The precursor composition has the basic characteristic of being solution-processable. The precursor composition does not contain a reducing agent. In specific embodiments, the organoamine is a primary monoamine.

In one embodiment, the sensing electrode comprises more than 50 atomic percent (at %) palladium oxide. In other embodiments, the sensing electrode comprises more than either 80 at % or 90 at % palladium oxide. The atomic percentage is the ratio of atoms of one kind to another. The palladium oxide may be formed together with the palladium during the thermal decomposition of the solution-deposited palladium precursor composition.

Different processes for making the pH sensor are contemplated. As described above, the sensing electrode can be made by solution coating the electrolyte layer with the palladium precursor composition, then heating to form the sensing electrode made of palladium. Alternatively, a palladium film could be formed on a substrate such as silicon, glass, or plastic, then removed from the substrate and applied to the electrolyte layer. The insulator layer 103 can be independently joined, or can be joined together with the electrolyte layer 104. The counter electrode 105 can then be applied to form the pH sensor.

The counter electrode 105 can also be a palladium electrode. Alternatively, the counter electrode may be made from other electrically conductive materials as well. These materials can be for example, a thin metal film, a conducting polymer film, or a conducting film made from conducting ink or paste. Other examples of electrode materials include but are not restricted to aluminum, gold, silver, chromium, zinc, indium, conductive metal oxides such as zinc-gallium oxide, indium tin oxide, palladium oxide, indium-antimony oxide, conductive polymers such as polystyrene sulfonate-doped poly(3,4-ethylenedioxythiophene) (PSS-PEDOT), and conducting ink/paste comprised of carbon black/graphite. The counter electrode can be prepared by vacuum evaporation, sputtering of metals or conductive metal oxides, conventional lithography and etching, chemical vapor deposition, spin coating, casting or printing, or other deposition processes.

In particular embodiments, the palladium salt is palladium acetate and comprises about 5 wt % to about 30 wt % of the precursor composition. The organoamine is either octylamine or decylamine.

Palladium serves as a cheaper alternative to gold, both in acquisition and manufacture, and demonstrates better adhesion and mechanical strain resistance. In its precursor form, palladium can be printed into patterned electrodes. Palladium electrodes also demonstrate improved sensitivity, better reliability and a shorter response time than gold electrodes.

The electrolyte layer 104 may be a solid or a gel saturated with a stable ionic composition. Typical electrolyte layers are saturated with KCl or $AgCl_2$.

The counter electrode has a stable, well-defined electrochemical potential. Ideally, the counter electrode should have zero impedance, and the potential of the counter electrode should remain constant irrespective of the electrolyte composition. Besides the standard hydrogen electrode, the Ag/AgCl electrode is the most well-known reference electrode, consisting of a chlorinated silver wire in contact with an electrolyte. Other examples of counter electrodes include calomel (based on mercury), SCE, and Cu/CuSO$_4$.

The resulting pH sensors have several advantages: 1) simple structure design; 2) compatibility with miniaturization process; 3) improved sensitivity; 4) better reliability due to better adhesion and mechanical strain resistance of Pd metal; and 4) low manufacturing costs due to the lower costs of material (Pd vs. Au) and simpler fabrication process by printing.

Devices have been fabricated, showing high sensitivity, shorter response time, and very good reversibility, stability, and reproducibility. In embodiments, the sensor has a sensitivity of at least 40 mV/pH and a response time no longer than 200 seconds. In other embodiments, the sensor has a response time of no longer than 100 seconds or no longer than 60 seconds. In more specific embodiments, the sensor has a sensitivity of at least 50 mV/pH, or of at least 60 mV/pH, or of at least 70 mV/pH. In further embodiments, the sensor has a linearity of at least 95% in the pH range from 2 to 12, or a linearity of at least 99% in the pH range from 2 to 12, or a linearity of at least 99.9% in the pH range from 2 to 12. In yet further embodiments, the sensor has a linearity of at least 99.99% in the pH range from 4 to 10.

The sensitivity and the linearity of a device are obtained by plotting the potential as a function of the pH value. The slope is the sensitivity, and a higher sensitivity is indicated by a larger absolute slope. The linearity is the $r^2$ value when fitting the data points to a linear equation.

The pH sensor may be used as part of a wearable medical device for continuous monitoring of complex health conditions and patients undergoing treatments. The device may include the pH sensor, a preamplifier, and an analyzer/transmitter. Other instruments can also be part of the medical device.

The following examples are for purposes of further illustrating the present disclosure. The examples are merely illustrative and are not intended to limit devices made in accordance with the disclosure to the materials, conditions, or process parameters set forth therein.

EXAMPLES

Example 1

A palladium precursor composition was prepared by dissolving 2.5 grams of palladium acetate into 6.0 grams octylamine and 1.5 grams toluene. After filtrating through a 0.2 μm syringe filter, the composition was coated on glass slides, then annealed at 195 degrees Celsius for about 2 to about 5 minutes to obtain conductive palladium films having a thickness of about 100 nanometers (nm). It should be noted that a small amount of palladium oxide can form when annealed in air. The palladium films could be used as an electrode.

A commercial TiO$_2$ nanoparticle dispersion in isopropanol was used to form a metal oxide layer on palladium electrodes by spin coating at 500-1000 rpm. The TiO$_2$ film was dried and baked at 200 degrees Celsius for 2 hours to condense the layer.

Vacuum evaporated Au electrodes (with 5-10 nm Cr adhesion layer) and silver electrodes (coated from commercial silver paste) with and without TiO$_2$ layers were prepared and used as controls to compare to the palladium electrode.

The electrodes were immersed in pH buffer solution along with a counter reference electrode comprising Ag/AgCl. The electrical potential (open circuit voltage) between the sensing electrode and the counter electrode was measured at different pH values of 4, 7, and 10. The results are presented in Table 1 below.

TABLE 1

| Sample | Sensitivity (mV/pH) | Linearity (%) | Reaction |
|---|---|---|---|
| Ag | — | — | No pH response; pH 4 and pH 10 gave a similar value while pH 7 was different |
| Ag + TiO$_2$ | 2 | 91.19 | Very little response |
| Au | 23 | 99.31 | Comparable response to literature results (26 mV/pH) |
| Au + TiO$_2$ | 24 | 90.54 | TiO$_2$ delamination from Au electrode |
| Pd | 41.2 | 95.10 | Good reversibility with repeatability; good stability and reproducibility, shorter response time than Au |
| Pd + TiO$_2$ | 45.6 | 99.10 | Improved sensitivity |

When silver was used as the electrode, no pH response was observed. After a metal oxide layer (TiO$_2$) was coated on silver, a small response was obtained. A gold electrode showed much better sensitivity than silver. However, gold is very soft, poorly adheres to substrates, and poorly adheres to metal oxides. Surprisingly, the palladium electrode had a high sensitivity of 41 mV/pH. The device also showed good reversibility; little to no change was observed during many cycles of sweeping from an acidic solution to basic solution, or backward from basic solution to acidic solution.

Figure 4:
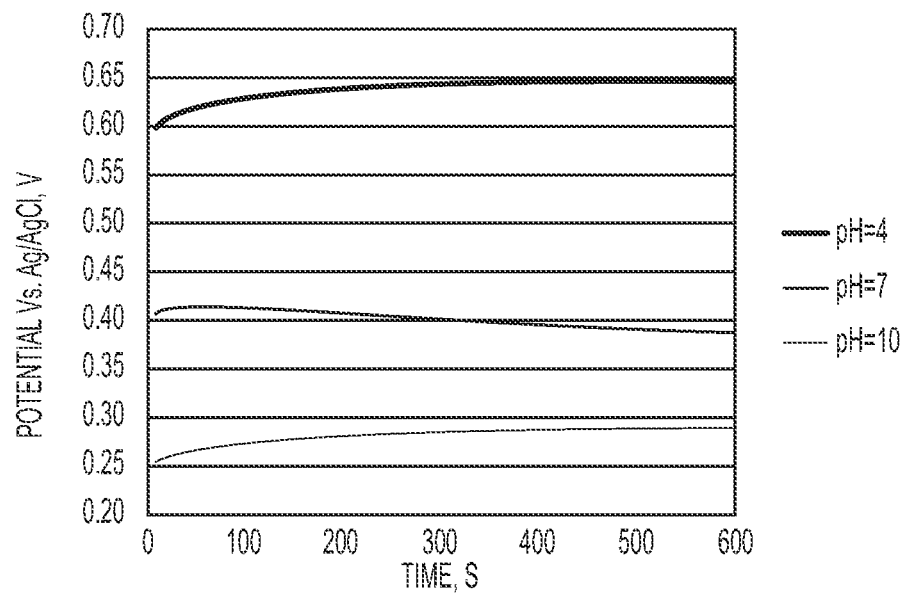
FIG. 4 is a graph of the electrochemical behavior of the palladium sensing electrode without metal oxide layer after dipping the electrode into buffer solutions of pH 4, 7, and 10.

FIG. 4 is a graph showing the potential versus time for palladium electrodes without a metal oxide layer. The response time, which is defined as the time required to achieve 90% of the maximum potential value, was about 200 seconds or less, about twice as fast as that of a gold electrode (about 400 seconds). The standard deviation was less than 10 mV. Addition of a TiO$_2$ layer further increased the sensitivity.

Example 2

The palladium precursor composition of Example 1 was was coated on glass slides heated to 200 and 250 degrees for different annealing times: 4 minutes, 24 hours and 48 hours. The amounts of PdO on the surface and in the bulk of the layer were detected using XPS analysis. The results of the sensitivity and linearity testing of the different electrodes is shown in Table 2 below.

TABLE 2

| No. | Annealing temp. | Annealing time | PdO on surface (%) | PdO in bulk (%) | Sensitivity (mV/pH) | Linearity |
|---|---|---|---|---|---|---|
| A | 200 | 4 min | 27.8 | 18.3 | 54.5 | 0.9988 |
| B | 200 | 24 hrs | 82.1 | 46.9 | 70.3 | 0.9995 |
| C | 200 | 48 hrs | 98.3 | 49.3 | 67.5 | 0.9994 |
| D | 250 | 4 min | 88.8 | 25.6 | 65.6 | 0.9995 |
| E | 250 | 24 hrs | 96.6 | 49.3 | 58.8 | 0.9993 |
| F | 250 | 48 hrs | 99.9 | 53.0 | 65.0 | 0.9996 |

Figure 5:
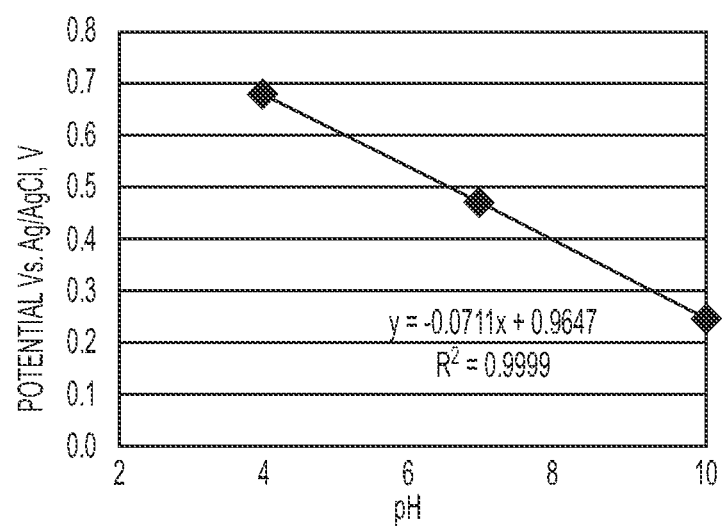
FIG. 5 is a graph of the typical pH response of the palladium sensing electrode with a titanium oxide layer at different pH values.

As seen in Table 2, the amount of PdO increased with an increase in annealing time and in annealing temperature. pH sensors made using these electrodes were made and measured as well. High sensitivity and linearity were observed. A typical response, shown in FIG. 5, illustrates a high sensitivity of 71 mV/pH with an excellent linearity of 0.9999.

The present disclosure has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A pH sensor comprising:
   (a) a sensing electrode;
   (b) a counter electrode;
   (c) an electrolyte layer located between the sensing electrode and the counter electrode; and
   (d) a metal oxide layer located between the sensing electrode and the electrolyte layer, the metal oxide layer being made of $TiO_2$, $ZnO$, $WO_3$, $SnO_2$, $RuO_2$, $Ta_2O_5$, or $IrO_2$;
   wherein the sensing electrode consists of palladium formed by thermal decomposition of a palladium precursor composition.

2. The pH sensor of claim 1, wherein the electrolyte layer is in physical contact with the sensing electrode and the counter electrode.

3. The pH sensor of claim 1, wherein the counter electrode comprises silver and silver chloride.

4. The pH sensor of claim 1, wherein the sensor has a sensitivity of at least 40 mV/pH.

5. The pH sensor of claim 1, wherein the sensor has a response time of no longer than 200 seconds.

6. The pH sensor of claim 1, wherein the sensor has a linearity of at least 95% in the pH range from 2 to 12.

7. The pH sensor of claim 1, wherein the sensor further comprises an insulator located adjacent to the electrolyte layer and between the sensing electrode and the counter electrode.

8. A biomedical device comprising a pH sensor comprising:
   (a) a sensing electrode;
   (b) a counter electrode;
   (c) an electrolyte layer located between the sensing electrode and the counter electrode; and
   (d) a metal oxide layer located between the sensing electrode and the electrolyte layer, the metal oxide layer being made of $TiO_2$, $ZnO$, $WO_3$, $SnO_2$, $RuO_2$, $Ta_2O_5$, or $IrO_2$;
   wherein the sensing electrode comprises palladium and palladium oxide.

9. The biomedical device of claim 8, wherein the sensing electrode comprises more than 50 at % PdO.

* * * * *